United States Patent [19]

Young

[11] Patent Number: 5,129,891
[45] Date of Patent: Jul. 14, 1992

[54] CATHETER ATTACHMENT DEVICE

[75] Inventor: Thomas M. Young, North Andover, Mass.

[73] Assignee: Strato Medical Corporation, Beverly, Mass.

[21] Appl. No.: 595,172

[22] Filed: Oct. 10, 1990

Related U.S. Application Data

[63] Continuation-in-part of Ser. No. 354,614, May 19, 1989, Pat. No. 5,041,098.

[51] Int. Cl.⁵ .............................................. A61M 25/00
[52] U.S. Cl. ..................................... 604/283; 604/905; 604/175; 285/238; 285/361
[58] Field of Search ............... 604/905, 256, 283, 175; 128/912; 285/238, 360, 361, 376, 396, 4.1, 402

[56] References Cited

U.S. PATENT DOCUMENTS

| | | | |
|---|---|---|---|
| 2,907,591 | 10/1959 | Gulick | 285/361 X |
| 3,585,654 | 6/1971 | Jacobs | 285/361 X |
| 4,033,613 | 7/1977 | Bram | 285/184 |
| 4,296,949 | 10/1981 | Muetterties et al. | 285/18 |
| 4,673,394 | 6/1987 | Fenton, Jr. et al. | 604/175 |
| 4,735,442 | 4/1988 | Bürli | 285/175 |
| 4,834,719 | 5/1989 | Arenas | 604/243 |
| 4,929,236 | 5/1990 | Sampson | 604/175 |
| 4,929,243 | 5/1990 | Koch et al. | 604/283 |
| 4,969,879 | 11/1990 | Lichte | 604/283 |
| 4,994,048 | 2/1991 | Metzger | 604/283 |
| 5,041,098 | 8/1991 | Loiterman et al. | 604/175 |
| 5,045,060 | 9/1991 | Melsky et al. | 604/93 |

Primary Examiner—John D. Yasko
Assistant Examiner—Adam J. Cermak
Attorney, Agent, or Firm—Lahive & Cockfield

[57] ABSTRACT

A connector for detachably securing an end of a tube, such as a catheter, to a fluid port of a fluid transfer assembly, such as an implantable device, the connector having a body part which defines a coupler for coupling to a coupler receiver of the transfer assembly. The connector includes a sleeve which fits within the body part and defines an aperture for compressively receiving an end of the tube which has been fitted over a fluid port of the transfer assembly. The body part is rotatable about the sleeve to facilitate coupling of the coupler and coupler receiver. In one embodiment, the connector further includes bayonet pins for twist locking the coupler in the coupling receiver. A tie down may be provided to prohibit the coupler from being inadvertently detached from the coupling receiver. A tactile indicator may be included to indicate correct coupling of the coupler and the coupler receiver. The sleeve generates a compressive force to secure the tube to the fluid port. A compression insert may be inserted between the sleeve and tube to provide a higher degree of compression of the tube upon the fluid port. In one embodiment, the tube is a catheter coupled to a patient and the fluid transfer assembly is an implantable device, for subcutaneous delivery of fluid to a patient in which the catheter and device have been implanted.

30 Claims, 5 Drawing Sheets

CATHETER ATTACHMENT DEVICE

This application is a continuation-in-part of U.S. pat. application Ser. No. 07/354,614, now U.S. Pat. No. 5,041,098, filed May 19, 1989.

BACKGROUND OF THE INVENTION

The present invention generally relates to the field of tube coupling devices, and more particularly, to a device for releasably attaching an end of a tube or catheter to a port of a fluid transport device.

Flexible tubes or catheters are often used with transport devices for fluid delivery systems. For example, numerous surgical and non-surgical treatment procedures require that a catheter be placed in fluid communication with a patient's vascular system. A number of devices for this purpose are known. Both implantable treatment reservoirs, such as disclosed in U.S. Pat. No. 4,673,394, and traditional cannula devices, afford access to a patient's vascular system, using catheters attached to those devices.

Such devices may also be used for blood transfer, for example, in hemodialysis. U.S. pat. application Ser. No. 354,614, now U.S. Pat. No. 5,041,098, assigned to the same assignee as the present application, discloses devices that are particularly adapted for this purpose. Flexible tubes are also used extra-corporeally to establish a desired fluid transport system. In the latter application, the tubes are often fit with connectors to permit flexibility in the assembly of a desired system from standardized components.

With regard to implantable vascular access devices of the prior art, catheters are typically permanently affixed to the implantable device prior to implantation. It is also known to use an implantable device which is adapted for attachment of a catheter to a chambered extension (i.e., a fluid exit or inlet port) of that device during the implantation procedure, but after the device is positioned within the patient. Typically, such catheters are adapted to be slidingly placed over a tubular port, and to be frictionally held in place.

In view of the nature of the Procedures by which implantable treatment devices are surgically implanted in patients, it is necessary that the connection between a catheter and the implantable device be easily accomplished. This enables a surgeon to concentrate on the proper placement of the implantable device. Nevertheless, the friction fit and placement of the catheter has proven to require some degree of skill and patience during implantation.

Known connectors, such as, for example, a mere collar circumscribing the catheter and which fits over a tubular port projecting from the implantable device, often do not afford secure attachment. If the inner diameter of the collar does not properly correspond to the outer diameter of the catheter, either the collar will not fit over the catheter, or the collar will not generate a sufficient compressive force to secure the catheter to the port. With known assemblies, therefore, it is necessary to keep on hand a variety of connectors so that an appropriate connector can be selected and used which will specifically accommodate the particular catheter being connected.

U.S. Pat. No. 4,673,394 discloses a particularly effective arrangement for attaching a catheter to an implanted access device. That arrangement includes a twist-lockable (bayonet-type) coupler in which a pair of bayonet pins extend in opposite directions from the generally cylindrical outer surface of the coupler. The pins, together with the geometry of the coupler, may be slidingly positioned over the tubular port of the implant with a particular angular orientation, and then twisted so that the pins are captively held in place by portions of the implant which define a void region used to capture the pins.

Of course, care must be taken such that the action of twisting the bayonet-type coupler to lock the catheter to the implant does not cause the catheter to be damaged. Even with such care, torquing of the catheter should be avoided, since a twisted catheter may become partially blocked to fluid flow, or worse yet, especially in multiple lumen catheters, may become entirely blocked to fluid flow.

It is therefore an object of the present invention to provide an improved connector for securely attaching a flexible tube, such as a catheter, to a chambered extension, such as a tubular fluid exit or inlet port, of a fluid transfer assembly, such as an implantable fluid delivery device.

It is another object of the invention to provide a catheter-to-device connector which is easily installed, provides a frictional lock between the catheter and device and enables twist-lockable action between the connector and device without substantially twisting the catheter.

It is yet another object of the invention to provide a compression sleeve for use with a catheter connector to provide greater compressive interaction between the catheter and a fluid exit or inlet port of an implantable device.

SUMMARY OF THE INVENTION

These and other objects of the present invention are well met by the presently disclosed flexible tube connector. The connector provides easy and secure coupling of a flexible tube, such as a catheter, to a chambered extension of a fluid transfer assembly, such as a fluid exit or inlet port of an implantable fluid delivery device. The connector is configured so as to enable desired connection of the connector and assembly without causing an obstruction of the fluid flow path or damage to the tube.

The connector includes a generally cylindrical body part and a sleeve. The body part extends along a central axis; the interior of the connector body part defines a substantially cylindrical central aperture extending along the central axis, for receiving the sleeve. The sleeve exterior surface is slidably engaged to the body part interior along the central aperture. The body part engages over the sleeve, preferably in a captive manner, but remains rotatable about the central aperture and sleeve. The sleeve also defines a substantially cylindrical central aperture extending along the central axis, for compressively receiving a flexible tube (such as a catheter), which has been previously slidingly fit over an elongated fluid port (such as of an implantable device). The connector is provided with a locking element on the connector body (such as a T-shaped flange) and a mating receiver on the fluid transfer device (such as a generally T-shaped void region defined by a peripheral flange).

The sleeve assures compressive securing of the tube to the fluid port. In this aspect of the invention, when the sleeve is fitted over the joined tube and the fluid port, a compressive force is generated to secure the tube to the outer surface of the fluid port, while the slideable cooperation of the exterior of the sleeve and the interior of the body part permits locking interaction of the body part's locking element and a mating receiver on an implantable access device without detrimental twisting or torquing of the tube.

One aspect of the invention is adapted for use with an implantable device, such as that described in U.S. Pat. No. 4,673,394. That implantable device includes a tubular exit port extending from its periphery. The port at one end is surrounded by a generally T-shaped void region defined by a peripheral flange, which mates with the generally T-shaped connector connecting element.

In use, the catheter is fitted over the tubular fluid port of the implant and the sleeve is forced over this catheter/port conjunction to compress the resilient catheter against the port. The T-shaped coupling of the body part now is twisted about the central axis to mate that element with the T-shaped void region receiver of the implant device. This assures secure and leak-free coupling of the catheter and access port. The rotatable cooperation of the body part and sleeve assures that the body part can be turned about its central axis to effect twist-locking of the connector and implant device without torquing or twisting of the catheter. Such torquing or twisting may otherwise dangerously abuse the fluid flow path; or damage the catheter.

In a preferred embodiment, opposed wing-like elements radially project from each side of the connector body part. The wing elements are preferably adapted to be tied down to the implant to permit the coupled connector to be secured to the implant so as to prevent inadvertent decoupling. A tactile indicator may be provided to indicate to the surgeon that correct coupling of the connector and device has been made.

The present invention may further include a compression insert, preferably tapered in cross-section, which, when inserted between the sleeve and catheter, affords further compression of the catheter against the port. This provides a greater degree of assurance that the catheter and fluid port connection will be leak-free.

BRIEF DESCRIPTION OF THE DRAWING

These and other features and advantages of the present invention will be more fully understood by reference to the following detailed description in conjunction with the attached drawing in which like reference numerals refer to like elements and in which.

DETAILED DESCRIPTION OF PREFERRED EMBODIMENTS

Figure 1:
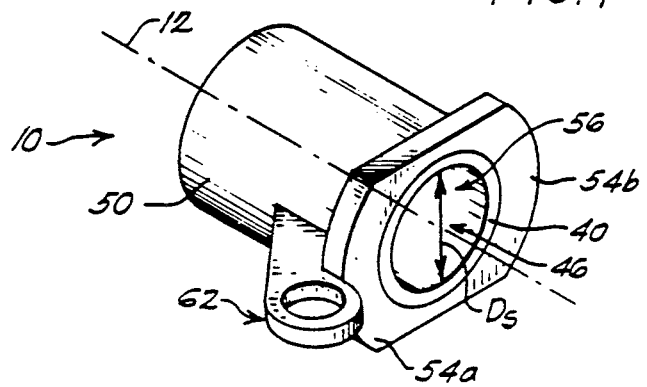
FIG. 1 is a perspective view of an embodiment of a connector embodying the present invention.

FIG. 1 is a perspective view of a connector 10 in accordance with the present invention, showing general cooperation of a cylindrical compression sleeve 40 (having an inner diameter $D_s$) fitted within a body part 50. Body part 50 is provided with extensions, such as pins or wing elements 54a, 54b, and, along with sleeve 40, generally forms a general T-shaped coupler 12 for coupling with a generally T-shaped coupler receiver of a cooperating fluid transfer device.

Figure 2:
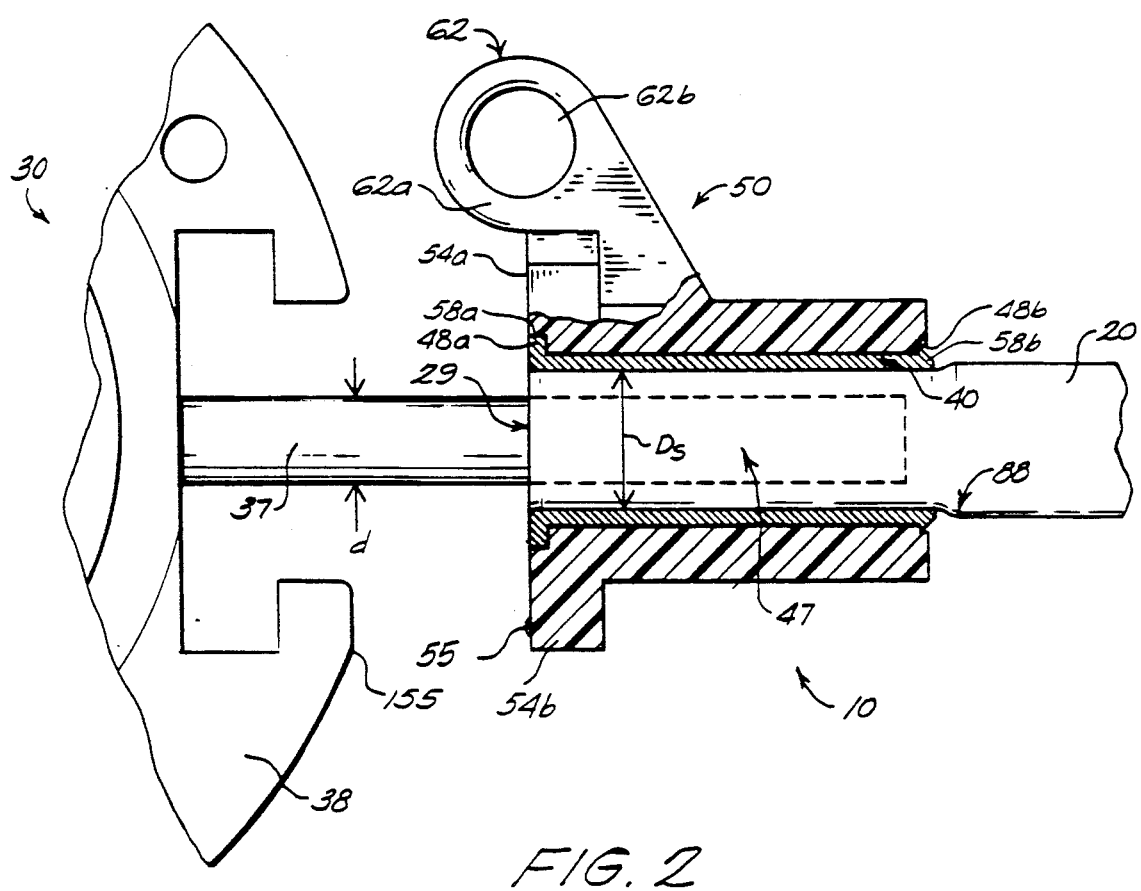
FIG. 2 is a cross-sectional view of the connector of FIG. 1 coupled over a prior art catheter fitted on a fluid port of a prior art implantable vascular access device.

FIG. 2 is a top cross-sectional view of connector 10 about to secure the proximal end 29 of a flexible vascular catheter 20 to a tubular fluid port 37 (having an outer diameter d) extending from an implantable vascular access device 30 of the type generally shown in U.S. Pat. No. 4,673,394. The distal end (not shown) of catheter 20 is positioned at a desired position in the patient's vascular system.

Figure 4:
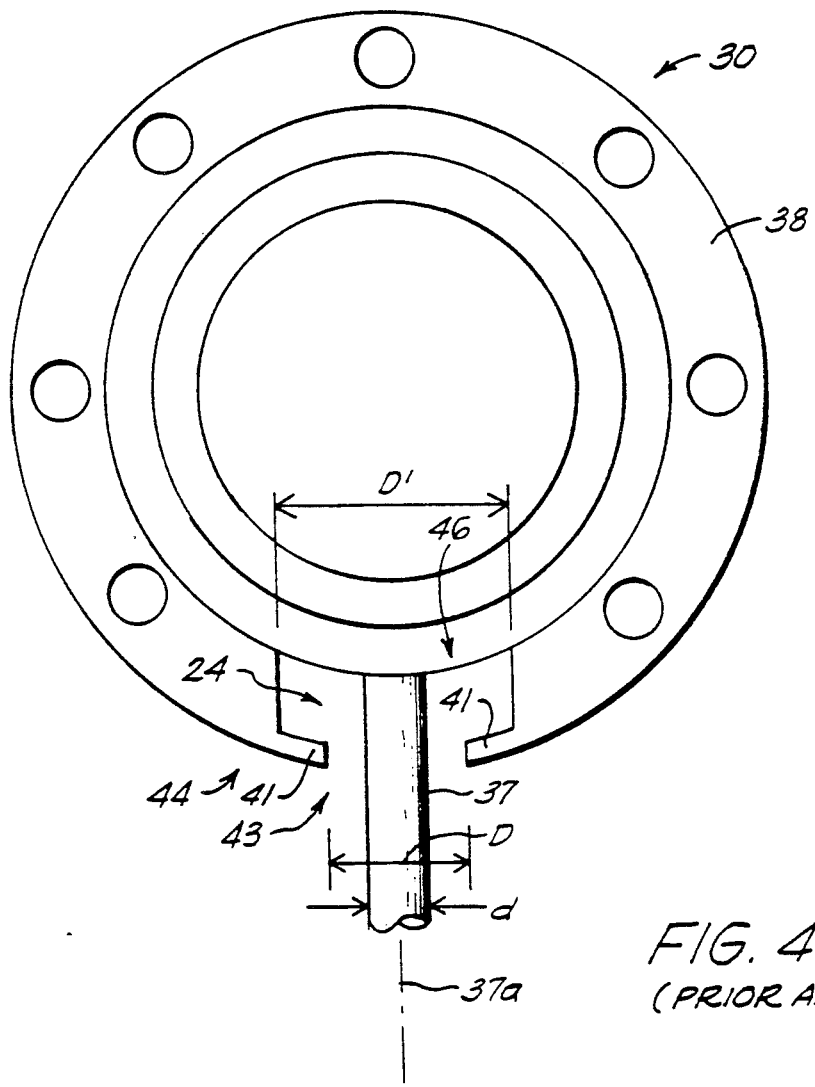
FIG. 4 is a bottom view of the prior art implantable device of FIG. 3.
Figure 3:
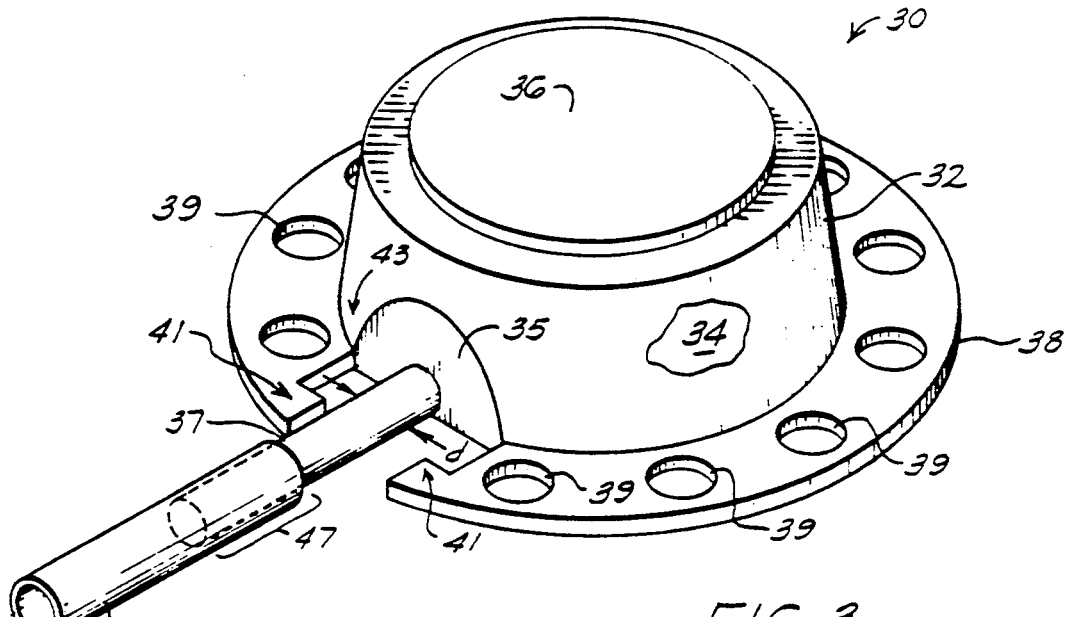
FIG. 3 is a perspective view of the prior art implantable vascular access device of FIG. 2.

In one embodiment, a cooperating fluid transfer device takes the form of an implantable vascular access device 30 as shown in the perspective view of FIG. 3 and the bottom view of FIG. 4. Device 30 preferably includes a device housing 32 which defines an internal generally cup-shaped reservoir cavity 34, e.g., for holding treatment fluids or medicine. Device housing 32 has an open face which is closed off by a cover 36. Tubular fluid flow or fluid exit (or inlet) port 37 extends out radially from wall 35 of device housing 32 along port axis 37a. The interior of port 37 is coupled directly to cavity 34.

Cover 36 is formed of a self-resealing polymer, which is preferably an elastomer such as silicone, rubber or latex, and is adapted to permit access to the reservoir cavity 34 using a hypodermic needle. Hence, in use, a hypodermic needle may be employed to puncture cover 36 to deliver a treatment fluid to reservoir cavity 34. The treatment fluid is then delivered to catheter 20 coupled to the tubular port 37 (having outer diameter d, where d is less than $D_s$) of device 30, whereby the fluid is provided to the vascular system of the patient. Device 30 may alternatively be configured to permit out-flow of body fluids, for example, blood in conjunction with a hemodialysis procedure. Device housing 32 is preferably formed of a biocompatible material, such as titanium or electro-polished 316L stainless steel or other surgical grade steel or other hard material such as DuPont Delrin(TM) or Teflon(TM).

A substantially planar, radially extending flange 38 circumscribes housing 32. Flange 38 includes an array of holes 39 spaced about the perimeter of housing 32, for use in suturing device 30 to a layer of the patient's tissue during the implantation procedure. Extension portions 41 of flange 38 extend on both sides of port 37. Preferably flange 38 and portions 41 define a generally T-shaped void region 24 disposed about port 37. More particularly, void region 24 comprises an axially extending portion 44 and a circumferentially extending portion 46. The axial portion 44 has a width D and the circumferential portion 46 has a width greater than D. Flange 38 and portions 41 and void region 24 thus form a T-shaped twist-locking receiver 43 whose function is further set forth below.

A leak-free and secure fit is required between the resilient catheter proximal end 29 and the rigid tubular port 37. However, the difficulty of forcing catheter end 29 over tubular port 37, particularly in the restricted environment of a subcutaneous installation, requires such cooperation that the catheter end 29 slides onto port 37 with some ease. As a result, this eased coupling may not be so tight as to be leak free, or worse, may permit inadvertent disconnection.

Furthermore, the tightness of fit between the catheter and port in the past has been accompanied by a twisting of the catheter as it is forced over the port. This twisting often distorted the catheter and partly obscured the passage of fluid within the catheter. This problem is magnified when a multiple lumen catheter is employed: such catheters are more sensitive to correct alignment with a cooperating multiple lumen port, and the difficulty of obtaining correct alignment makes their secure and leak-free interconnection problematic. The present invention solves this problem.

Figure 5:
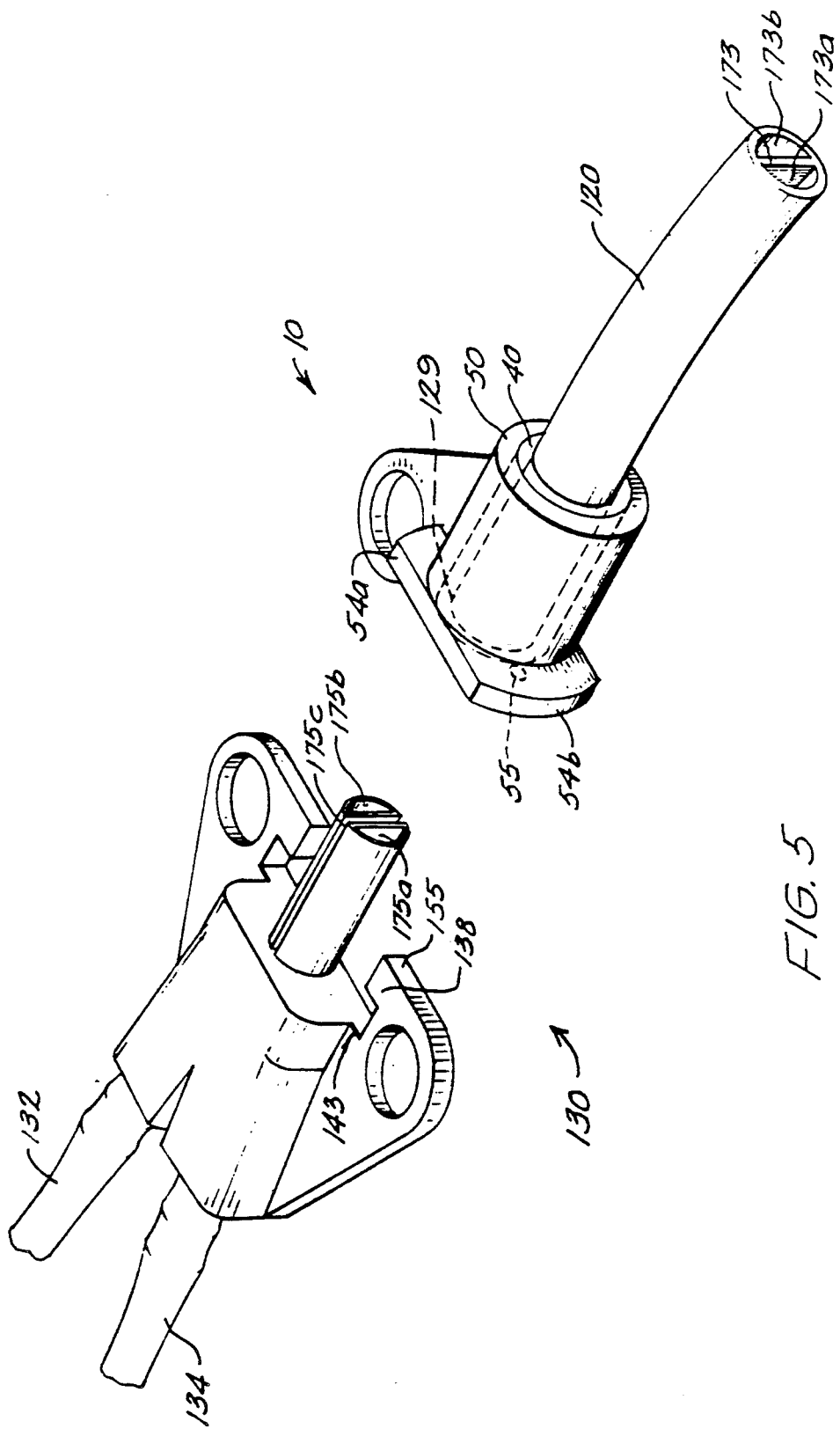
FIG. 5 is a perspective view of an alternative embodiment of the present invention adapted for coupling a dual lumen catheter to a dual lumen fluid transfer device.

By way of example, an alternative fluid transfer device 130 and associated catheters 132 and 134 are shown in FIG. 5, together with a connector 10 embodying the invention. Device 130 is adapted to couple each of catheters 132 and 134, through one of ports 175a and 175b to a respective lumen 173a, 173b of a dual lumen catheter 120 having a proximal end 129. Catheter 120 includes an internal divider 173 which creates the two lumens 173a, 173b internal to the catheter. The two ports 175a and 175b of device 130 are separated by a gap 175c, each port being adapted to receive one of the lumens 173a, 173b of catheter 120 for transport of multiple fluids from/to a multiple lumen transport device 130. Gap 175c is so configured as to receive catheter divider 173 as the catheter is fitted over the ports. The need for proper alignment and coupling of the respective catheter lumen and ports 175a and 175b is therefore self-evident. (It will be further appreciated, however, that the present invention applies equally well in use with a single, multiple lumen catheter and like single multiple lumen port.)

Toward these ends, for example with respect to the devices of FIGS. 2 and 5, connector device 10 of the present invention provides compression sleeve 40 to assure a leak-free and secure fit of the catheter end 29 over port 37 (FIG. 2) or end 129 over ports 175a and 175b (FIG. 5). The compression sleeve is substantially rigid relative to the substantially flexible catheter. Hence, the resilient catheter can be reasonably sized for tight but comfortable placement over port 37 (or ports 175a and 175b). The connector device 10 is first positioned so that sleeve 40 extends about end 29 (or 129) of the catheter 20 (or 120) and then this entire assembly is slidingly placed over port 37 (or ports 175a and 175b). Alternatively, the catheter can first be slidingly placed over port 37 (or ports 175a and 175b) without, or with minimal, twisting, and then compression sleeve 40 is slidingly placed over the catheter/port conjunction. The rigid sleeve supplies a higher degree of compression between the joined tube and port to assure a leak-free connection that will not easily or inadvertently disconnect.

Body part 50 defines a generally arcuate smooth inner glide surface, i.e., cylindrical central aperture 56. The outer surface of compression sleeve 40 defines a generally arcuate smooth glide surface, i.e., an exterior generally cylindrical outer contour 48 configured to cooperate with the body part central aperture 56. Sleeve 40 further defines a generally arcuate smooth-walled orifice, i.e., a generally cylindrical central aperture 46 for compressive receipt of catheter 20. Aperture 46 is of an internal diameter which causes compression of the catheter as the sleeve is slid over the surface of the catheter up to and over the catheter/port conjunction 47, as enabled by the resilient character of the catheter material (typically a plastic or elastomer).

As seen in FIGS. 1, 2, and 5, body part 50 at its central aperture 56 is fitted over compression sleeve 40 in a closely cooperating manner, thus capturing sleeve 40. However, since sleeve 40 compressively secures the proximal end 29 of catheter 20 to port 37, the sleeve essentially is fixed in the axial direction relative to the catheter. Therefore, body part 50 at its central aperture 56 must slidingly engage the outer surface 48 of sleeve 40 so that it can be twisted into locking cooperation at receiver 43 of device 30 without causing the sleeve and catheter to be twisted. Hence, it is intended that body part 50, as so mounted on sleeve 40, may be freely rotated about the relatively fixed sleeve.

Figure 6:
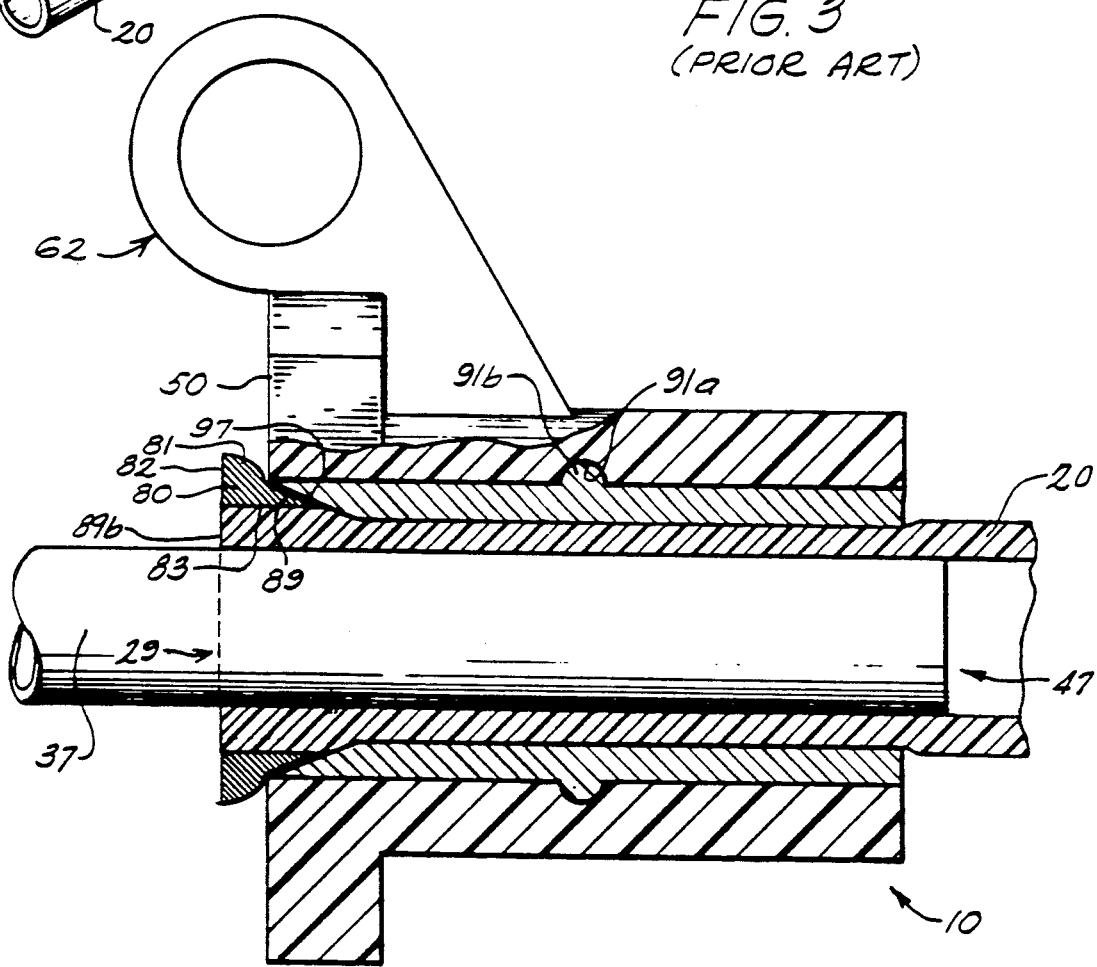
FIG. 6 is a cross-sectional view of an alternative embodiment of the invention installed over a catheter fitted over a fluid access port, but before being mated with a cooperating twist-locking receiver of a fluid transfer device.

In a preferred embodiment, body part 50 includes inset grooves 58a, 58b, and sleeve 40 includes raised flanges 48a, 48b, whereby body part 50 is installed over sleeve 40 with flanges 48a, 48b mating with grooves 58a, 58b, respectively. Now, when connector 10 is being mated with and locked into device 30, sleeve 40 is prevented from slipping away rom its location over catheter 20 and catheter/port conjunction 47, while body part 50 can still be rotated about sleeve 40 during such mating. This groove/flange combination permits body part 50 to be forced over sleeve 40 after the latter has been fitted into its desired compression location over the catheter/port conjunction 47. In an alternative embodiment of connector 10, an example of which is shown in FIG. 6, only a single groove 91a and single flange 91b are provided for interlocking of body part 50 and sleeve 40. The locations of the flanges on sleeve 40 and grooves on part 50 could be reversed in yet other embodiments. Still other variations by which the sleeve 40 is captively held by body part 50 are also within the scope of the present invention.

In any event, it now will be appreciated that the relatively non-torqueable interaction of sleeve 40 and catheter/port conjunction 47 is unaffected when body part 50 is torqued to lock bayonet flanges 54a, 54b into the cooperating receiver 43 of device 30. Thus connector 10 can tightly secure catheter 20 (120) to port 37 (or ports 175a and 175b) of device 30 (130) against unwanted leakage or disconnection, and the entire connection is secured against unwanted disconnection by means of the T-shaped lock mechanism, without unwanted twisting or torquing of the catheter.

It should be understood, however, that in the context of the invention, "T-shaped" refers to any reasonable shape having a width on the perimeter of the flange 38 which is smaller than the width at the end of the void region 24 which is distal to the flange perimeter. An alternate example of such an opening would be a dovetail-shaped opening. Furthermore, it will now be appreciated that while other frictional or threaded coupling of connector 10 and device 30 is also within the scope of the present invention, a preferred T-shaped interconnection is shown and described herein.

An optional feature of the invention, as shown in FIG. 2 or 5, includes a confirmation mechanism for indication of correct coupling of connector 10 and the fluid delivery device. The mechanism may include a contact spot or protrusion 55 on connector body part 50 and a cooperating contact spot or lip 155 of the flange of the fluid delivery device. In this manner, a "tactile" or "click"-type indication of correct placement can be felt by the surgeon as the body part wing elements 54a, 54b are properly seated in the receiver of the fluid delivery device. Hence it will be appreciated that contact devices 55, 155 are designed to interact only when the T-shaped connector is properly locked in secure and mating cooperation in the T-shaped receiver of the delivery device.

In addition to the foregoing, a securing device 62 is provided on connector 10 to prevent inadvertent detachment of the connector from the delivery device. Securing device 62 may include a flange 62a which is an extension of body part 50. Flange 62a internally defines a tie down hole 62b. Tie down hole 62b permits suturing the body part perhaps to one of the plurality of holes 39 in flange 38 of device 30, for example, after connector 10 is properly connected to device 30.

It will now be appreciated that proper installation of sleeve 40 over catheter/port conjunction 47 requires selection of a sleeve with an inner diameter greater than the outer diameter of the port and less than the outer diameter of the catheter after the catheter is installed on tube 37. This normally assures adequate compression of the catheter.

Figure 7:
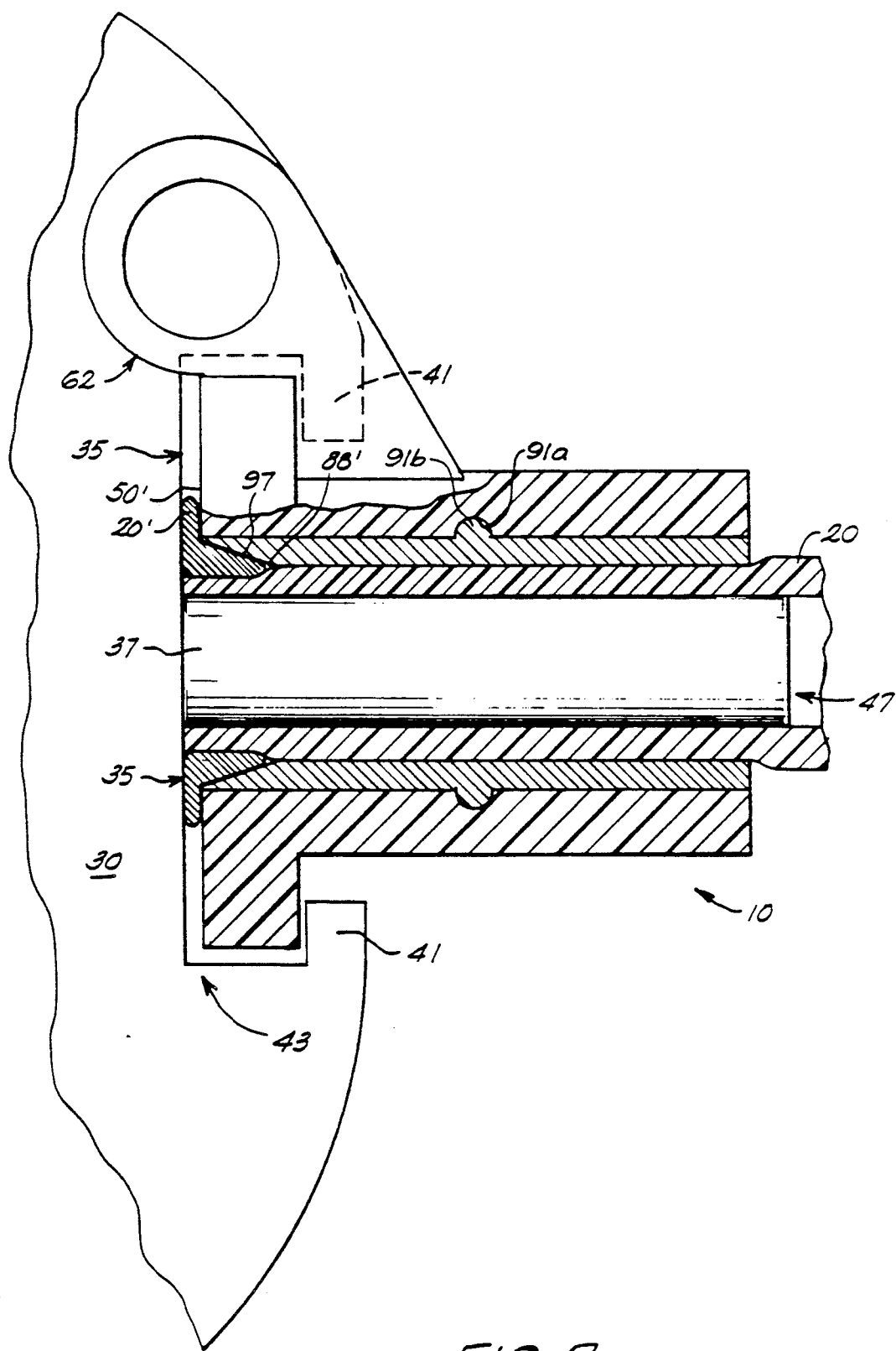
FIG. 7 is a cross-sectional view of the connector embodiment of FIG. 6 and a partial view of a fluid transfer device after the connector is mated with the twist-locking receiver of the fluid transfer device.

Notwithstanding the foregoing, further assurance of leak-free sealing at catheter/port conjunction 47 may be desired. Hence, as shown in FIG. 6, an insert 80 provides for tight coupling of the catheter/port conjunction 47. In one embodiment, insert 80 is a generally cylindrical sleeve, which in cross-section, as shown in FIG. 6, is generally wedge-shaped, and is formed from a material which is compressible between device 30 and connector 10. The insert defines an outer surface 81, an abutment surface 82, an inner surface 83, and an insertion end 89. In this embodiment, sleeve 40 is preferably provided with an inclined edge 97 which defines a tapered annular entryway for receipt of cooperatively tapered surface 81 of insert 80. In this manner, as connector 10 is locked into the twist-locking receiver 43 of device 30 the inclined edge 97 of the sleeve annular entryway compresses the insert and forces the abutment surface 82 of the insert against wall 35 of device 30, as well as around and into catheter 20, as shown in FIG. 7. Hence, insert 80 provides an extra degree of leak-free compressive sealing between catheter 20 and device 30.

In use of insert 80, preferably connector 10 is first placed over catheter 20 to overlie the catheter end 29. Then the compressible insert 80 is placed over end 29 of catheter 20. Now insert 80 and catheter 20 together with connector 10 (sleeve 40 and body part 50) are slid over port 37, with the catheter end 29 extending up toward wall 35 of device 30. The body part 50 of connector 10 is then twist-lock coupled with device 30. The action of forcing connector 10 into locked interconnection with device 30 forces compression surfaces 81, 83 between sleeve 40 and catheter 20 and forces a portion of insert 80 between wall 35 and faces 50′ of body part 50 and 20′ of catheter 20 to further seal the catheter's connection to device 30.

In an alternative embodiment, insert 80 may be formed as a split ring of a material similar to that of sleeve 40, having an inner diameter greater than the catheter inner diameter and less than the catheter outer diameter. The split face 80x of a split insert 80 is shown in FIG. 7.

Because device 30 is intended to be sutured directly to the patient, a high degree of maneuverability of device 30 and accessibility of suture holes 39 is desired to facilitate the surgical process of implantation. Additionally, because device 30 connects directly, via catheter 20, to the patient's vascular system, the integrity of the connection between the catheter and the device must be assured. Moreover, in order to reduce risk of harm to the patient, it is preferred that the catheter be moved minimally during and after placement of the catheter distal end within the vascular system.

It is therefore desirable, in practice of the invention, to first position and affix device 30 to the patient, then insert the distal end of the catheter to the desired patient location, then size the length of the catheter 20 by cutting its proximal end 29, and then frictionally couple the catheter proximal end 29 over tubular port 37 of device 30. Sleeve 40 is forced over the catheter/port conjunction 47, and then catheter 20 is secured to device 30 by a T-shaped coupler, formed by body part 50 mounted on sleeve 40, and T-shaped receiver 43 of device 30. The tactile aid of the confirmation mechanism (devices 55 and 155) signals correct and complete connection of connector 10 and device 30. Preferably, connector 10 is secured in its coupled cooperation with device 30 by suturing the body part securing device 62 (at securing hole 62b) to a hole 39 of flange 38.

The sleeve and body Part need not be formed from biocompatible material if not to be implanted. They may be formed of DuPont Delrin(TM) (acetal resin), thermoplastic, metal (such as titanium), DuPont Teflon (TM) (polytetrafluoroethylene), or a mixture of nylon and polyethylene, as their use may dictate. The compression seal, for example, may be a split ring formed of the above materials or, as a soft compressible ring, of silicone, polyurethane, butyl rubber, or ethylene propylene.

It will be understood that the above description pertains to only several embodiments of the present invention. That is, the description is provided by way of illustration and not by way of limitation. For example, while the port and catheter are described and shown having particular diameters, connoting a circular cross-section, an oval or other non-circular cross-section is equally within the scope and teaching of the present invention. Therefore, for ease of description, the term diameter used in this document will also be understood to connote an analogous cross-sectional dimension of non-circular cross-section parts. Nevertheless, the scope of the invention is to be defined according to the following claims.

What is claimed is:

1. Connector apparatus for coupling an end of a resilient tube about the exterior of a tubular extension of a fluid transfer assembly, said extension extending along a port axis and having an outer diameter d, said connector apparatus comprising:

A. a rigid tubular sleeve extending along a reference axis, said sleeve having an inner diameter $D_s$, where Ds is greater than d, and B. a rigid body part disposed about said tubular sleeve and associated capture means for capturing said sleeve within said body part, whereby said sleeve is freely rotatable about said reference axis with respect to said body part, wherein said body part further includes twist lock means responsive to coaxial alignment of said port axis and said reference axis and to subsequent rotation of said body part about said reference axis and said port axis, for selectively engaging said body part to a fluid transfer assembly having a tubular extension, when said sleeve is coaxial with and positioned about said tubular extension.

2. The connector apparatus of claim 1 wherein said tube has a nominal inner diameter which is less than d, and said tube has a nominal outer diameter which is greater than Ds when said tube is expanded to have an inner diameter equal to d, and wherein said sleeve is adapted to captively hold said tube end to said tubular extension when said body part is engaged to said fluid transfer assembly.

3. The connector apparatus of claim 1 wherein said body part comprises a connector mating means for mating with a cooperating transfer assembly such that said connector apparatus is adapted for interlocking coupling to said cooperating transfer assembly.

4. The connector apparatus of claim 3 wherein said connector mating means comprises a pair of flanges and said transfer assembly comprises a pair of flange receivers, whereby said pair of flanges is cooperable with said pair of receivers to selectively interlockingly couple said connector apparatus and said transfer assembly.

5. The connector apparatus of claim 4 wherein said connector mating means includes a T-shaped portion of said body part and said cooperating transfer assembly includes a receiver defining a T-shaped void region formed on the periphery of said fluid transfer assembly.

6. The connector apparatus of claim 3 wherein said body part comprises at least one wing element which extends out from said body part to form said connector mating means.

7. The connector apparatus of claim 6 wherein at least one of said wing elements comprises a tie down means for enabling tying down said body part to prevent disconnection of said connector apparatus for a fluid transfer assembly to which it has been connected.

8. The connector apparatus of claim 3 wherein said body part has a central axis and further comprises a first retention assembly and said sleeve comprises a second retention assembly, such that when said body part is fitted over said sleeve, said first and said second retention assemblies cooperate to retain said body part over said sleeve while enabling said body part to rotate about its central axis over said sleeve.

9. The connector apparatus of claim 8 wherein one of said first retention assembly and said second retention assembly comprises at least one groove and the other of said first retention assembly and said second retention assembly comprises at least one flange for fitting in said groove.

10. The connector apparatus of claim 3 wherein said fluid transfer assembly is an implantable fluid transfer device, said tubular extension is a fluid port of said implantable fluid transfer device, and said tube is a catheter.

11. The connector apparatus of claim 10 wherein said catheter has a plurality of lumens and said fluid port has a plurality of lumens within a discrete tube, whereby respective ones of said catheter lumens are adapted for coupling to respective ones of said fluid port lumens.

12. The connector apparatus of claim 3 further comprising confirmation means for confirmation of correct mating of said connector mating means and said cooperating transfer assembly.

13. The connector apparatus of claim 12 wherein said confirmation means comprises a respective contact part on each of said connector mating means and said cooperating transfer assembly, such that as said connector mating means and said cooperating transfer assembly are correctly mated, said respective contact parts contact and cause a tactile mating indication.

14. The connector apparatus of claim 1 wherein said body part has an inner diameter which is smaller at least in part than said outer diameter of said sleeve at least in part, such that said sleeve can be captured within said body part.

15. The connector apparatus of claim 1 wherein said body part has a central axis and further comprises a generally cylindrical body extending along said central axis, and wherein the interior of said body part defines a substantially cylindrical central aperture extending along said central axis for receiving said sleeve.

16. The connector apparatus of claim 15 wherein said sleeve exterior surface slidably engages said body part interior central aperture.

17. The connector apparatus of claim 16 wherein said sleeve defines a substantially cylindrical central aperture extending along said central axis for compressive receiving of a flexible tube which is positioned about a chambered extension of a fluid transfer assembly.

18. The connector apparatus of claim 17 wherein said fluid transfer assembly is an implantable fluid transfer device, said extension is a fluid port of the implantable fluid transfer device, and said tube is a catheter.

19. The connector apparatus of claim 1 further comprising a compression insert, said insert having an internal receiver means for receipt of said tube.

20. The connector apparatus of claim 19 wherein said insert is more resilient than said sleeve.

21. The connector apparatus of claim 20 wherein said insert is a split ring.

22. The connector apparatus of claim 20 wherein said insert is generally cylindrical and has a maximum outer diameter which tapers to a lesser outer diameter at one of the ends of said insert, wherein said insert presents an arcuate surface to said sleeve, wherein said surface is inclined with respect to the central axis of said insert at a predetermined angle.

23. The connector apparatus of claim 22 wherein one end of said insert comprises an abutment member for abutting against said fluid transfer assembly.

24. The connector apparatus of claim 23 wherein said sleeve further comprises a tapered annular insert receiver, for receipt of said insert, wherein said tapered receiver presents a conical surface generally inclined at said predetermined angle from its central axis.

25. The connector apparatus of claim 1 further comprising in combination said tubular extension of a fluid transfer assembly.

26. Connector apparatus for coupling an end of a resilient tube about the exterior of a tubular extension of a fluid transfer assembly, said extension extending along a port axis and having an outer diameter d, said connector apparatus comprising:

A. a rigid tubular sleeve extending along a reference axis, said sleeve having an inner diameter $D_s$, where $D_s$ is greater than d, and B. a rigid body part disposed about said tubular sleeve and associated capture means for capturing said sleeve within said body part, whereby said sleeve is freely rotatable about said reference axis with respect to said body part, C. a substantially annular compression insert, said insert having an external surface adapted for at least partial receipt within said sleeve, wherein said body part further includes twist lock means responsive to coaxial alignment of said port axis and said reference axis and to subsequent rotation of said body part about said reference axis and said port axis, for selectively engaging said body part to a fluid transfer assembly having a tubular extension, when said sleeve is coaxial with and positioned about said tubular extension, and when at least a portion of said insert is compressively held against the interior of said sleeve.

27. The connector apparatus of claim 26 wherein said compression insert is tapered from a first of its ends toward a second of its ends.

28. The connector apparatus of claim 26 wherein said fluid transfer assembly is an implantable fluid delivery device, said extension is a fluid port of said implantable fluid delivery device, and said tube is a catheter.

29. The connector apparatus of claim 26,
wherein said tube has a nominal inner diameter which is less than d, and said tube has a nominal outer diameter which is greater than Ds when said tube is expanded to have an inner diameter equal to d; and
wherein said sleeve is adapted to captively hold said tube end to said tubular extension when said body part is engaged to said fluid transfer assembly.

30. The connector apparatus of claim 26 further comprising in combination said tubular extension of a fluid transfer assembly.

* * * * *